United States Patent [19]
Dummitt

[11] Patent Number: 4,775,764
[45] Date of Patent: Oct. 4, 1988

[54] METHOD FOR PREPARING 4,4′ DIFLUOROBIPHENYL

[75] Inventor: William E. Dummitt, St. Louis, Mo.

[73] Assignee: Mallinckrodt Inc., St. Louis, Mo.

[21] Appl. No.: 78,616

[22] Filed: Jul. 28, 1987

[51] Int. Cl.⁴ ............................................. C02C 17/26
[52] U.S. Cl. ..................................... 570/140; 570/129
[58] Field of Search ................................ 570/140, 129

[56] References Cited

FOREIGN PATENT DOCUMENTS 2236364  2/1974  Fed. Rep. of Germany ...... 570/129
198428  11/1983  Japan ................................... 570/129
198427  11/1983  Japan ................................... 570/129

Primary Examiner—J. E. Evans
Attorney, Agent, or Firm—R. J. Klostermann; Goodwin L. N.; Veo Peoples

[57] ABSTRACT

An improved method for preparing 4,4′ difluorobiphenyl by reacting a parafluorinated Grignard reagent and a parafluorinated halophenyl in solution and in the presence of free palladium producing catalysts is disclosed.

11 Claims, No Drawings

METHOD FOR PREPARING 4,4′ DIFLUOROBIPHENYL

BACKGROUND OF THE INVENTION

The compound 4,4′ difluorobiphenyl has been long used as an insecticide and more recently, has found use as a monomer in the preparation of high performance polymers. The present invention is a new and improved method for this compound.

In the past, 4,4′-difluorodiphenyl has been prepared from 4,4′-biphenyl-bis-diazonium-piperidide (by diazotizing benzidine and coupling with piperidine) and concentrated hydrofluoric acid; by the action of sodium on para-fluorobromobenzene in either; from benzidine by tetrazotization and decomposing the biphenyl-bis-diazonium salt with concentrated hydrofluoric acid (and even ferric chloride has been present to stimulate this reaction); and by the prolonged contact of the vapors of fluorobenzene with a red hot wire. However, prior to the present invention, the most satisfactory method for making 4,4′-difluorobiphenyl was by far the method described by G. Schiemann and W. Winkelmuller, published in "*Organic Syntheses*", Collected Volume 2, Page 188". The reaction therein proceeds as depicted below:

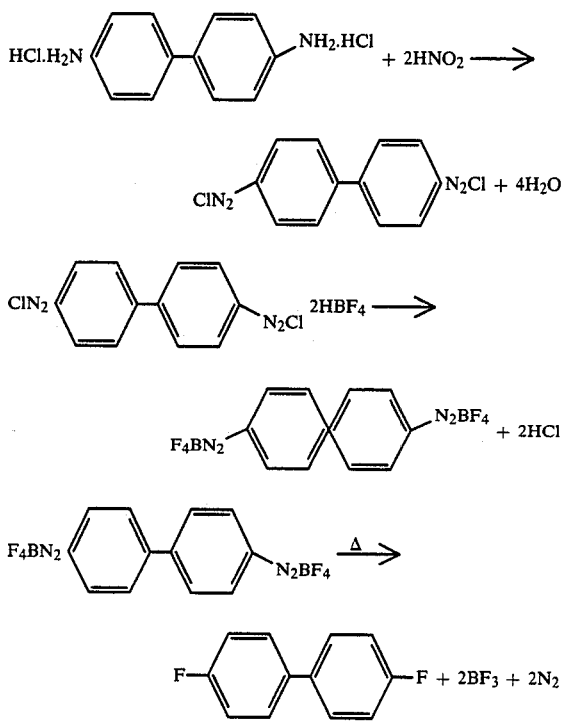

Commercial benzidine and concentrated hydrochloric acid are reacted to form the dihydrochloride. The benzidine dihydrochloride is tetrazotized and concurrently a mixture of boric acid and hydrofluoric acid is slowly added and stirred with a lead rod. A thick paste of 4,4′-biphenylene-bis-diazonium borofluoride forms. The product is collected and washed consecutively with alcohol and ether and dried. The product is decomposed with heat and the black residue is steam distilled to obtain a pure white compound to obtain the 4,4′-difluorobiphenyl in yields of 80 to 81% based upon the tetrazonium borofluoride, or 54 to 56% based upon the benzidine used. The raw materials for this reaction are inexpensive and the yields are commercially acceptable. However, the initial benzidine has become so highly regulated that it is practically unavailable for commercial use.

A facsimile method for synthesizing 4,4′-difluorobiphenyl is described by McKillop & Elsom, published in "*Tetrahedron*, Volume 26, Page 4041 (1970)". They describe the production of this compound in 77% yield from the magnesium Grignard of 4-bromofluorobenzene with thallium (I) bromide. Unfortunately, large quantities of toxic thallium compounds are produced as by-products and accordingly, this method is commercially unacceptable.

Accordingly, a relatively non-toxic reaction, from commercially available ingredients having either a low raw material costs and/or substantial commercial yields in the production of 4,4′-difluorobiphenyls would be a substantial advancement in the art.

SUMMARY OF THE INVENTION

It is an object of the present invention to provide an improved method for manufacturing 4,4′-difluorobiphenyls without diazotizing benzidine.

It is a further object of the present invention to provide a method for manufacturing 4,4′-difluorobiphenyl at commercial yields above 95%.

It is a further and additional object of the present invention to provide a method for manufacturing 4,4′-difluorobiphenyl from non-toxic materials.

These objects and others which will be apparent from the following detailed description of preferred embodiments are obtained by reacting a para-fluorinated Grignard reagent with a para-fluorinated halophenyl in the presence of a palladium catalyst which is convertible into palladium metal in the course of the reaction.

DETAILED DESCRIPTION OF THE PREFERRED EMBODIMENTS

In the process of this invention, para-fluorinated Grignard reagents reacted with para-fluorinated halophenyls in the presence of palladium catalysts surprisingly yielded above 95% 4,4′-difluorobiphenyl. Although palladium catalysts have been found to provide a high effect in preparing monofluorobiphenyls when reacting Grignard reagents and aryl halides, this reaction was found in the past to be unsuccessful with difluorobiphenyls, as for example, 2,2′-difluorobiphenyl. Additionally, given the expense of the raw materials involved, the resultant yields below 95% were commercially disappointing even for the monofluorobiphenyls. See, "*Palladium Metal-Catalyzed Cross-Coupling of Aryl Iodides With Aryl Magnesium Bromides. Syntheses of Fluorobiphenyls*", Journal of Organmetallic Chemistry, Volume 125 (1977), Pages 281–290. We have nevertheless surprisingly found that such palladium catalyzed Grignard exchange reactions between parafluorinated Grignard reagents and parafluorinated halophenyls provide a synergistic reaction yielding high purities and above 95% yields for 4,4′-difluorobiphenyl.

Parafluorinated aryl Grignard reagents having the formula

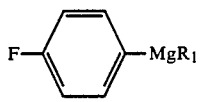

wherein $R_1$ is Br or I may be obtained from any commercial source or may be prepared by any known method. Preferably, the Grignard reagent is provided from the bromo compound because parafluorinated aryl magnesium bromide is soluble in ethers, whereas parafluorinated aryl magnesium iodide is not, however, the process or method of this invention may proceed with either raw material.

The preferred method for manufacturing the Grignard reagent consists of reacting parafluorinated bromo benzene with magnesium in the presence of tetrahydrofuran.

The parafluorinated halophenyl of the present invention having the formula

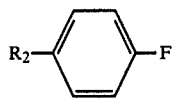

wherein $R_2$ is Br or I may likewise be prepared from any known method or may be obtained from any of many available commercial sources. Preferably, the parafluorinated halophenyl of the present invention is parafluoroiodobenzene and is preferably reacted with the parafluorophenyl magnesium bromide to provide 4,4'-difluorobiphenyl plus magnesium iodobromide.

Although it is an essential embodiment of the present invention that one of the reactants be an iodinated compound, the iodine may either be present with the Grignard reagent or with the substrate which adds to the Grignard reagent.

Although ethers, such as tetrahydrofuran, ethyl ether, diisopropyl ether, etc., are convenient for preparing the parafluorinated Grignard because Grignard reactions work best in ethers, other organic solvents may also be employed.

The reaction of the parafluorinated Grignard and the parafluorinated halophenyl preferably proceeds in a solvent. Although it is not essential that the same solvent be employed in this reaction as is employed in preparing the Grignard, it may be desirable to do so. In fact, the reaction can be conducted however in a wide variety of solvents, including for example, ethers, hydrocarbons, non-halogenated aromatics, dichloromethane, chloroform, or other chlorohydrocarbons.

The preparation of the Grignard reagent and the main reaction of the invention are both exothermic. They can be run at any temperature above room temperature up to the boiling point of the solvent, however, it is preferred that the reactions be run at reflux temperatures.

The preferred stoichiometry for the method of the present invention is to use a 1:1 mole to mole ratio of the Grignard reagent to the parafluorinated halophenyl. However, excesses of either reactant can still be employed and will provide good yields of 95% and more based upon the limiting reagent.

The amount of palladium catalyst can be varied over a wide range. As little as 1 part per million of palladium chloride may be used based upon the limiting reagent, however, larger amounts can be used without harming the reaction. Although palladium II chloride is preferred, any palladium catalyst which produces palladium metal during the course of the reaction may be employed as for example, palladium sulfate, palladium acetate, palladium bromide, palladium iodide, palladium fluoride, palladium metal, and others.

It is particularly preferred within the process of this invention for exceptional yields that the product of the reaction mixture be acidified prior to product recovery. It is believed that such acidification may dissolve various magnesium salts that otherwise create unwanted by-products and/or reduce product yield.

It is particularly preferred to add to the product of the reaction mixture, an additional solvent for recovery of the product in which the 4,4'-difluorobiphenyl is highly soluable, as for example dichloro-methane. This is believed to permit the reaction to run at higher, more commercially acceptable, concentrations.

Other embodiments of the invention which may generally come within the disclosure above described are within the contemplation of the invention. The following example is submitted to be illustrative of the present invention.

EXAMPLE I

In 75 ml. of dry tetrahydrofuran were stirred 17.48 grams parabromofluorobenzene (100 mm.), 2.64 grams (108 mg-atom) magnesium turnings, and 1 mg. palladium (II) chloride. The Grignard reagent parafluorophenyl magnesium bromide formed in approximately 30 minutes. Then, 22.2 grams parafluoroiodobenzene (100 mm.) was added and the mixture refluxed for 1 hour. The reaction mixture was added to water. The water was acidified with hydrogen chloride. Then, 100 ml. dichloromethane was added. The aqueous layer was drained, leaving a tetrahydrofuran/dichloromethane layer containing the product in solution. Filtrations and evaporation of solvent yielded 18.26 grams of the product 4,4'-difluorobiphenyl (96%).

What is claimed is:

1. A method for making 4,4' difluorobiphenyl having the formula

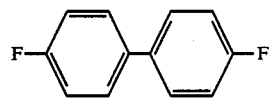

comprising the steps of:
(a) preparing parafluorinated Grignard reagent having the formula

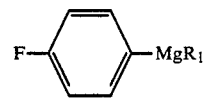

wherein $R_1$ is Br or I; and
(b) preparing a parafluorinated halophenyl having the formula

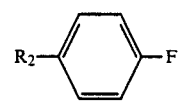

wherein $R_2$ is Br when $R_1$ is I or I when $R_1$ is Br (c) reacting in an organic solvent the products of steps (a) and (b) where only $R_1$ or only $R_2$ is I in the presence of a palladium catalyst selected from the group consisting of palladium chloride, palladium sulfate, palladium acetate, palladium bromide, palladium iodide, palladium fluoride, and palladium metal.

2. The method of claim 1 wherein the palladium catalyst is palladium (II) chloride.

3. The method of claim 1 wherein compounds of step (a) and (b) are in stoichiometric amounts.

4. The method of claim 1 wherein the compounds of either step (a) or step (b) are used in excess.

5. The method of claim 1 wherein the reaction is conducted in a solvent.

6. The method of claim 5 wherein the reaction is conducted at reflux.

7. The method of claim 5 wherein the solvent is selected from the group consisting of ethers, hydrocarbon, nonhalogenated aromatics and chlorohydrocarbons.

8. The method of claim 5 wherein the reaction is conducted in tetrahydrofuran.

9. The method of claim 1 or 2 wherein the reaction mixture is refluxed, added to water, and acidified prior to product recovery and evaporated to purification.

10. The method of claim 1 or 2 wherein a solvent in which 4,4'-difluorobiphenyl is highly soluble is added for purposes of product recovery.

11. The method of claim 9 wherein a solvent in which 4,4'-difluorobiphenyl is highly soluble is added for purposes of product recovery.

* * * * *